(12) United States Patent
Satsutani et al.

(10) Patent No.: US 6,251,245 B1
(45) Date of Patent: Jun. 26, 2001

(54) DETECTING AND ANALYZING APPARATUS FOR POSITIVE IONS AND NEGATIVE IONS IN A LIQUID

(75) Inventors: Taisuke Satsutani, Kobe; Eiji Nishi, Amagasaki, both of (JP)

(73) Assignee: Kobe Denpa Kabushiki Kaisha, Kobe (JP)

(*) Notice: Subject to any disclaimer, the term of this patent is extended or adjusted under 35 U.S.C. 154(b) by 0 days.

(21) Appl. No.: 09/426,415

(22) Filed: Oct. 25, 1999

(30) Foreign Application Priority Data

Oct. 28, 1998 (JP) ................................. 10-306967

(51) Int. Cl.[7] .................................................. G01N 27/26
(52) U.S. Cl. .......................... 204/416; 204/408; 204/400
(58) Field of Search ................................... 204/400, 416, 204/408

(56) References Cited

U.S. PATENT DOCUMENTS 4,172,777 * 10/1979 Yamamoto et al. ................. 204/406
4,447,398 * 5/1984 Schwartz et al. .................... 422/102

FOREIGN PATENT DOCUMENTS 61-083955 * 4/1986 (JP).

OTHER PUBLICATIONS

CAPLUS abstract of Murai et al. (JP 61083955 A2), Apr. 1986.*

* cited by examiner

Primary Examiner—T. Tung
Assistant Examiner—Alex Noguerola
(74) Attorney, Agent, or Firm—Marshall, O'Toole, Gerstein, Murray & Borun

(57) ABSTRACT

The present invention provides an apparatus which divides ions present in a liquid in a small amount into positive ions, negative ions, and charge density, measures the divided ions and the charge density, and displays amounts thereof. The apparatus further includes a storing function of data thereof. The apparatus has a signal detecting section 21 having a sensor section 5 disposed in an upper portion of a body 1, a signal detecting box A disposed in a lower portion of the body 1, and including therein a hoisting and lowering bench which moves a container C in which liquids to be measured are held to and from the sensor section 5, and a measuring body B for processing a signal output from the signal detecting section 21, detecting and displaying in accordance with an amount of ions, and for outputting impressed voltage to recording function of data and the sensor section.

4 Claims, 5 Drawing Sheets

DETECTING AND ANALYZING APPARATUS FOR POSITIVE IONS AND NEGATIVE IONS IN A LIQUID

BACKGROUND OF THE INVENTION

1. Field of the Invention

The present invention relates to a detecting and analyzing apparatus for positive ions and negative ions present in a liquid, and more particularly, to a detecting and analyzing apparatus for positive ions and negative ions in a liquid, that is capable of measuring positive ions, negative ions, and charge density which are present only in a small amount in the liquid.

2. Description of the Related Art

Contamination of air and water is becoming significant as the living environment changes. However, no evaluation method for determining such contamination is available.

In the case of running water, although quality and testing criteria are issued, even if one drinking water sample satisfies such testing criteria, this sample can be insufficient in terms of a taste evaluation. In particular, even if certain running water supplies satisfy the issued criteria as a drinking water, some supplies may be good in taste, and other supplies may be bad in taste. Such a difference is caused by a difference of raw water source, a difference in purification process (e.g., difference in the sequence of the process steps, difference in application timing of a process agent, and the like), a difference in degree or kind of contamination of the raw water source, a difference in minerals present in the raw water source, and the like.

Further, in recent years, drinking water is processed by various means to meet quality criteria, but water evaluation is insufficient. This is because the water is analyzed based on its pH, electrical conductivity, chemical components, and the like.

As described above, water contains a variety of materials, and water processing methods differ. Therefore, recently, it has become necessary, in some cases, to use a water-purification device, or an alkali ion water-purification device, rather than drinking the running water as supplied, or it is necessary to further purify waterworks water. For these reasons, waterworks water in its as-supplied state is not satisfactory as drinking water, and good tasting water and safe water are required.

Further, water quality differs depending upon the water source, and taste also differs depending upon the water source. Therefore, recently, water other than drinking water also is activated to provide functional water, or impurities are strictly eliminated from water to make super purified water, and such water frequently is used in accordance with common usage.

In such circumstances, when water is processed to improve its functionality, and when difference in taste is inspected, the functionality cannot be improved effectively and, in many cases, the difference cannot be attributed only from a pH test of water using a pH meter, an electrical conductivity test of water using an electrical conductivity meter, or a chemical analysis for individual components in the water.

According to the present invention, ions present only in a small amount in a liquid are divided into positive ions, negative ions, and liquid charge density, and are measured. It is an aspect of the present invention to provide a detecting and analyzing apparatus for positive ions and negative ions in a liquid, which is capable of displaying the measured values, and storing data concerning the measured values.

SUMMARY OF THE INVENTION

A detecting and analyzing apparatus for positive ions and negative ions in a liquid of the present invention comprises:
- a sensor section having a collector electrode,
- a signal detecting section for outputting a signal which is proportional to an amount of ions in the liquid contacting the collector electrode,
- a container for accommodating the liquid to be measured, and
- a measuring body, wherein
  - the measuring body processes the signal output from the signal detecting section, thereby displaying in accordance with an amount of detected ions, storing data of detected ion amount, and outputting impressed voltage to the sensor section.

According to the invention, voltage, waveform, frequency, and the like of impressed voltage for the sensor in the detecting and analyzing apparatus are varied and used, and it is possible to check a degree of collection of positive ions and negative ions in the liquid. With this feature, it is possible to check, stepwise, what kind water is easily treated, and what kind of water is easily made as good taste water.

According to the invention, it is possible to measure trace quantities of positive ions, negative ions, and charge density present in any kind of water. Any kind of water includes, 1) long-standing water of a first embodiment, which exists in various locations, while always changing its appearance,
2) water having components which vary largely depending upon its source,
3) water prepared artificially and including chemical components or the like, and it becomes further difficult to check the water quality depending upon the analysis and the like of the chemical components, and
4) water in which measured values often vary and it is very difficult to repeat the measurements of the components because the water greatly includes gas, the water is evaporated at its surface and gas in the air enters the water.

With such a measurement, it is possible to indicate the cause of water activation and nature of taste in water in terms of amount from a direction different from chemical measurements which are divided to various current elements.

A concrete structure of the detecting and analyzing apparatus for positive ions and negative ions in a liquid of the present invention comprises:
- a signal detecting box including therein a sensor section having a coaxial cylindrical structure disposed in an upper portion of a body, a signal detecting section for outputting a signal which is proportional to an amount of ions in the liquid contacting a collector electrode, and a hoisting and lowering bench disposed in a lower portion of the body for hoisting and lowering the container in which liquids to be measured are accommodated with respect to the sensor section, and
- a measuring body for displaying in accordance with an amount of detected ions, storing data of detected ion amounts, and outputting impressed voltage to the sensor section.

It is preferable that the signal detecting box and the body of the measuring body constituting the apparatus are both constructed of a metal.

Preferably, the detecting and analyzing apparatus includes a means for controlling a temperature of the liquid to be measured.

For example, the sensor section of the signal detecting box is disposed in the upper portion of the body such that the sensor section directs downward, and the hoisting and lowering bench is moved up and down by rotating a knob mounted to the hoisting and lowering bench.

It is desirable that the detecting and analyzing apparatus is provided in its body of the measuring body with an amplifying circuit of the detected signal, a digital data display circuit, a data record outputting circuit, an impressed voltage generating section for the sensor, a zero-correction adjusting circuit, a sensitivity adjusting circuit, a measurement starting circuit, an automatic/manual switching circuit, and an impressed voltage switching circuit for a manually operating sensor.

In the detecting and analyzing apparatus for positive ions and negative ions, for example, a zero adjustment is performed in air before a liquid to be measured is placed on the hoisting and lowering bench. Thereafter, the hoisting and lowering bench is lowered and the container (beaker) in which the liquid, i.e., the object to be measured, is contained, is placed on the hoisting and lowering bench. Then, the knob is rotated to hoist the hoisting and lowering bench, thereby inserting an ion detecting section of the sensor into the liquid in the container, and the hoisting and lowering bench is stopped at a predetermined position.

The power of the measuring body is turned on, and the measurement starting switch is turned on. Then, the measurement is automatically started, and measurements of positive ions, charge density in the liquid, and negative ions are performed repeatedly at arbitrary constant intervals. During measurement, when a value exceeds a measurement range, the digital display displays thereon "over." At that time, the sensitivity is adjusted by the sensitivity changeover switch and digitally displayed. For example, during the measurement of functional water, ordinary waterworks water or the like, if great difference does not appear in the measured value, the automatic measurement is switched to manual measurement. Then, the measurement time is changed, or the waveform, frequency or voltage of impressed voltage of the sensor is changed. With this operation, it is possible to measure the water corresponding to the difference in liquid quality.

These objects as well as other objects, features and advantages of the present invention will become more apparent to those skilled in the art from the following description with reference to the accompanying drawings.

DESCRIPTION OF THE PREFERRED EMBODIMENT

An embodiment of the present invention will be explained based on the drawings below.

Figure 1:
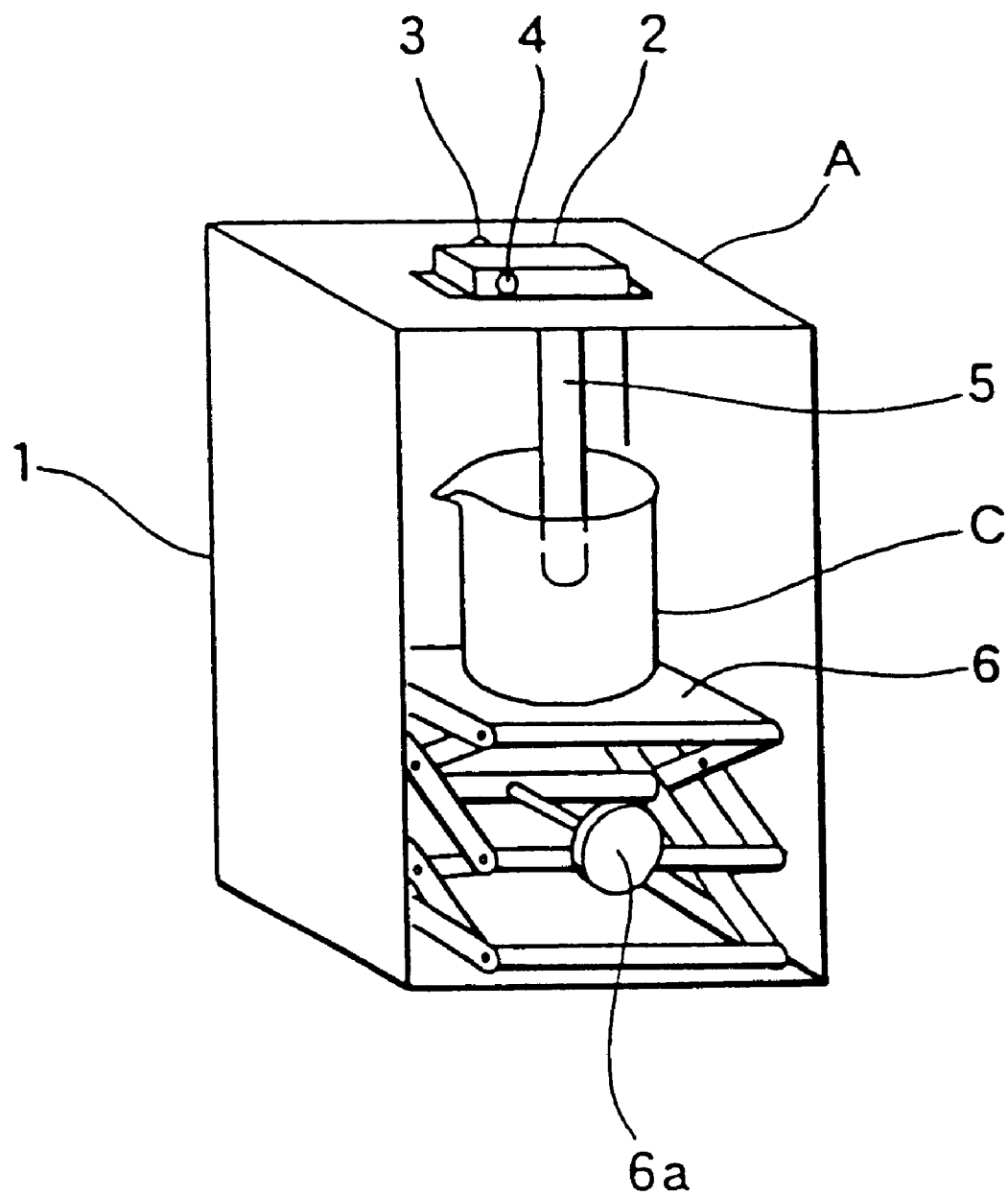
FIG. 1 is a perspective view of a signal detecting box constituting a detecting and analyzing apparatus for positive ions and negative ions present in a liquid according to one embodiment of the present invention.
Figure 2A:
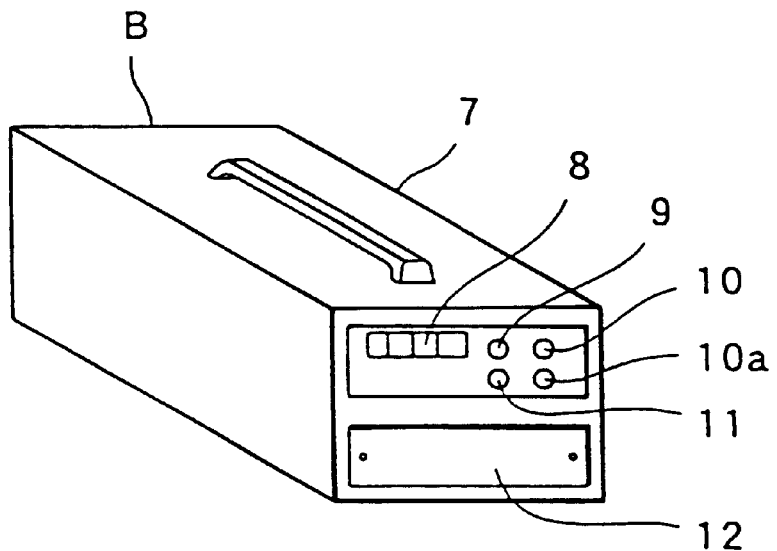
FIG. 2A is a perspective view showing a front side of a measuring body constituting the detecting and analyzing apparatus for positive ions and negative ions present in a liquid of an embodiment of the invention.
Figure 2B:
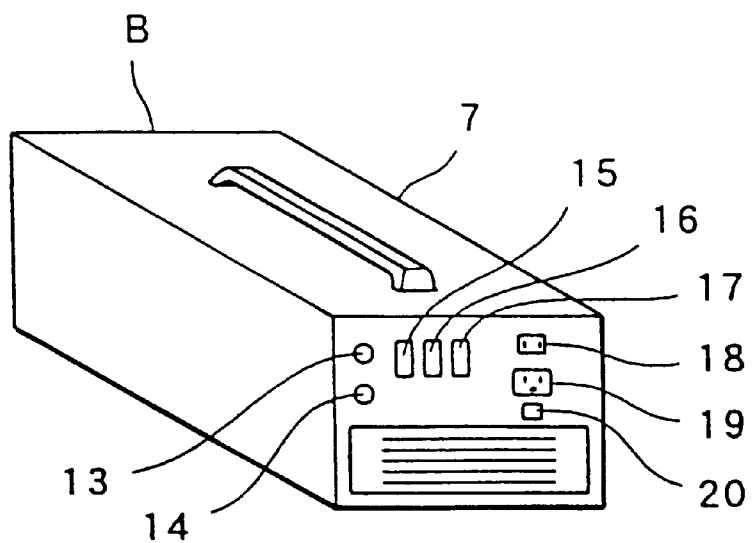
FIG. 2B is a perspective view showing a back side of the measuring body.
Figure 3:
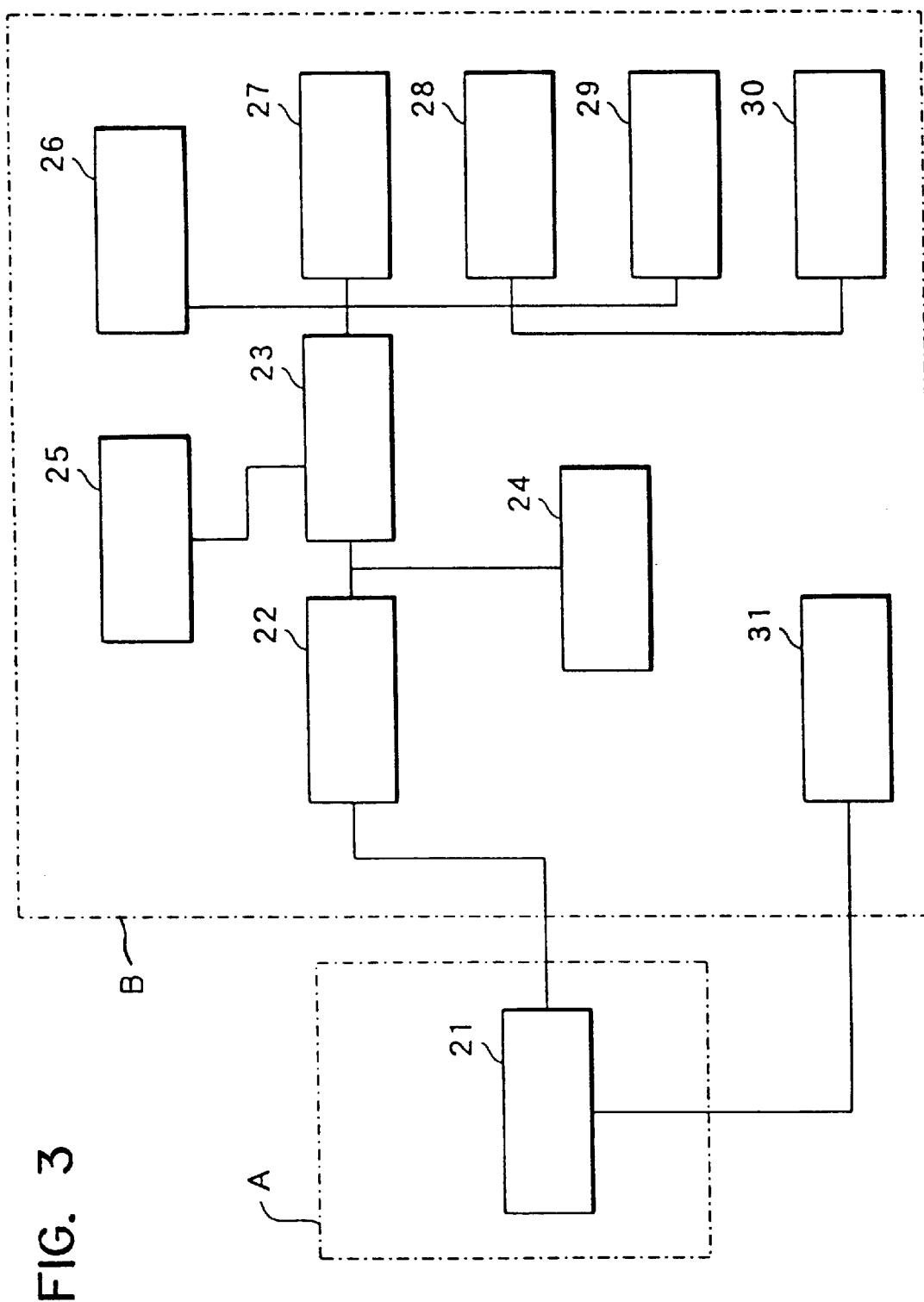
FIG. 3 is a schematic circuit diagram of the detecting and analyzing apparatus for positive ions and negative ions present in a liquid in an embodiment of the invention.

FIG. 1 is a perspective view of a signal detecting box constituting a detecting and analyzing apparatus for positive ions and negative ions present in a liquid in one embodiment of the present invention. FIG. 2A is a perspective view showing a front side of a measuring body constituting a detecting and analyzing apparatus for positive ions and negative ions present in a liquid in another embodiment of the invention, and FIG. 2B is a perspective view showing a back side of the measuring body. FIG. 3 is a schematic circuit diagram of the detecting and analyzing apparatus for positive ions and negative ions present in a liquid in an embodiment of the invention.

In FIG. 1, a body 1 of a signal detecting box A is constructed of metal.

A sensor-fixing box 2 is disposed on an upper portion of the body 1. Outside body 1, box 2 is provided at its side surface with a signal connector 3 and an impressed voltage output connector 4. A sensor section 5 is suspended from a lower surface of box 2 within body 1. Sensor 5 is provided with a collector electrode (not shown).

A hoisting and lowering bench 6 is disposed in body 1 such as to be opposed to sensor section 5. A container C, i.e., a beaker for accommodating the sample to be measured therein, is placed on hoisting and lowering bench 6. Hoisting and lowering bench 6 moves up and down by rotating a knob 6a added thereto.

Hoisting and lowering bench 6 has a temperature control device to control temperature of a liquid to be measured in container C, which is not illustrated in drawings. The temperature control device has a heater and a temperature sensor to detect temperature of the sample. According to the temperature data measured by the temperature sensor, the temperature of the sample is varied and controlled by varying an impressed voltage of the heater or heating period.

In FIGS. 2A and 2B, a body 7 of the measuring body B is constructed of metal.

Body 7 is provided at its front surface with a digital display section 8 for displaying measured values, a measurement starting switch 9, a sensitivity changeover switch 10, a manual sensor impressed voltage changeover switch 10a, a zero correction volume 11, and a sensor impressed voltage generating section 12. Body 7 is provided at its rear surface with an impressed voltage outputting connector 13, a signal inputting connector 14, a personal computer communication connector 15, a printer connector 16, a power switch 17, an AC outputting connector 18, an AC inputting connector 19, and a case ground terminal 20.

As shown in FIG. 3, the detecting and analyzing apparatus comprises an I/V converter 22 for converting a detected signal which is proportional to an amount of positive ions and negative ions detected by a signal detecting section 21 of the signal detecting box A into voltage, and a signal amplifying section 23. The detecting and analyzing apparatus can measure correctly by a zero correcting section 24 for zero-correcting before measurement, and a sensitivity changeover section 25 for adjusting the sensitivity in accordance the input signal.

By operating a measurement starting section 26 (measurement starting switch is turned ON), a measured value output from the signal amplifying section 23 is displayed by a digital display section 27, a personal computer communication recording section 28, and a printer recording output section 29. If a normal measurement is carried out automatically by switching an automatic/manual switching section 30, measurements of positive ions, charge density in liquid and negative ions are repeated at arbitrary constant intervals. Here, when the measurement is carried out with an arbitrary polarity for arbitrary time, the measurement can be carried out manually by changing over the automatic/manual switching section 30. A sensor impressed voltage generating section 31 can also check for idiosyncrasies of the liquid by varying impressed voltage, waveform, and frequency in accordance with nature of the liquid.

FIGS. 4 and 5 are graphs of experiments showing experimental examples of three kinds of water of the present invention. In each of the drawings, (+) represents positive ion current, (−) represents negative ion current, and (S) represent charge density current in water.

Figure 4A:
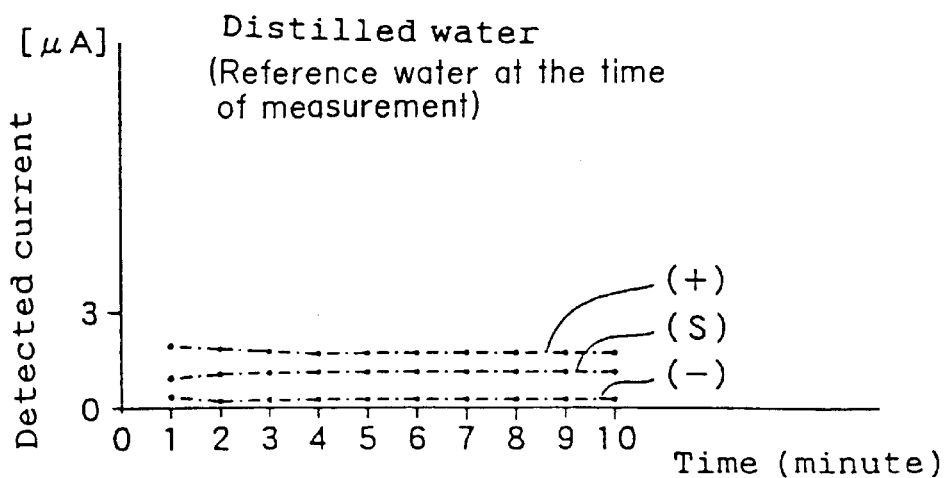
FIG. 4 is a graph of an experiment showing an experimental example of the invention.
Figure 4B:
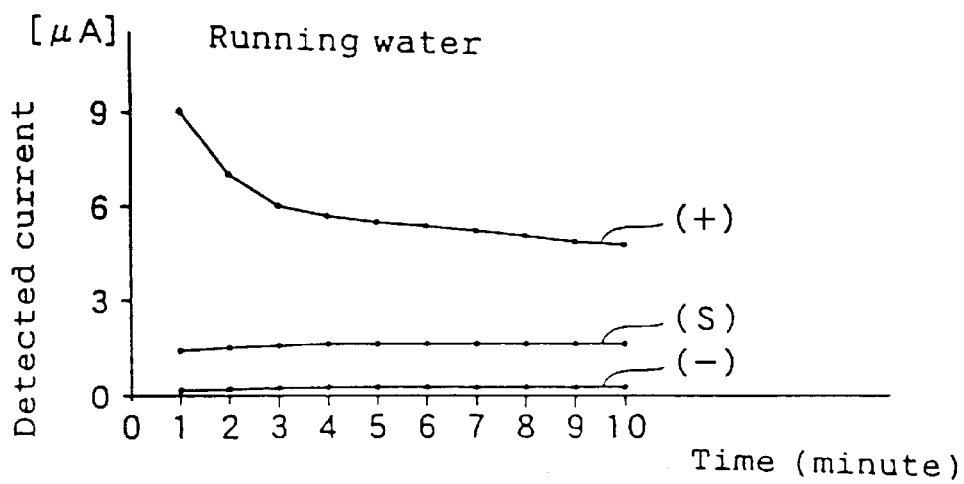
Figure 4C:
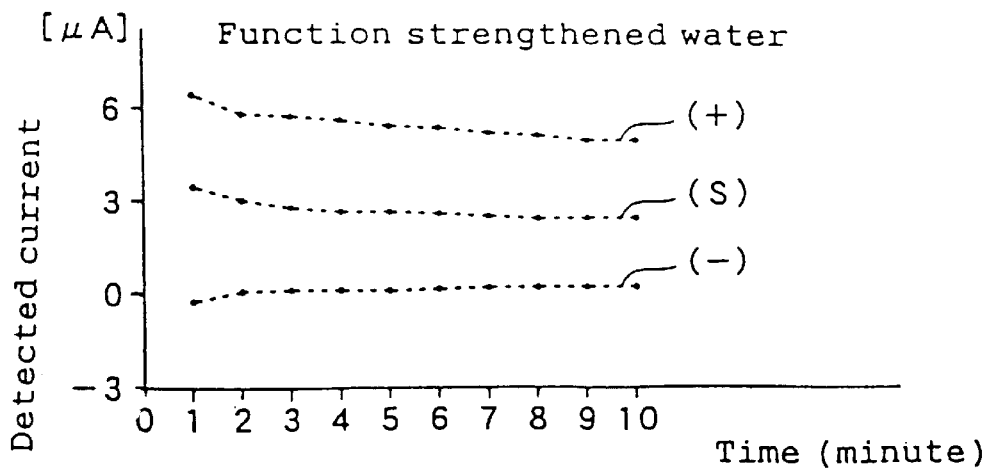

FIG. 4 shows results of measurements of distilled water as reference water (FIG. 4A), running water (FIG. 4B), and water whose function is strengthened (FIG. 4C). As apparent form FIGS. 4A, 4B and 4C, differences in balance of positive ions and negative ions of water could be detected.

Figure 5A:
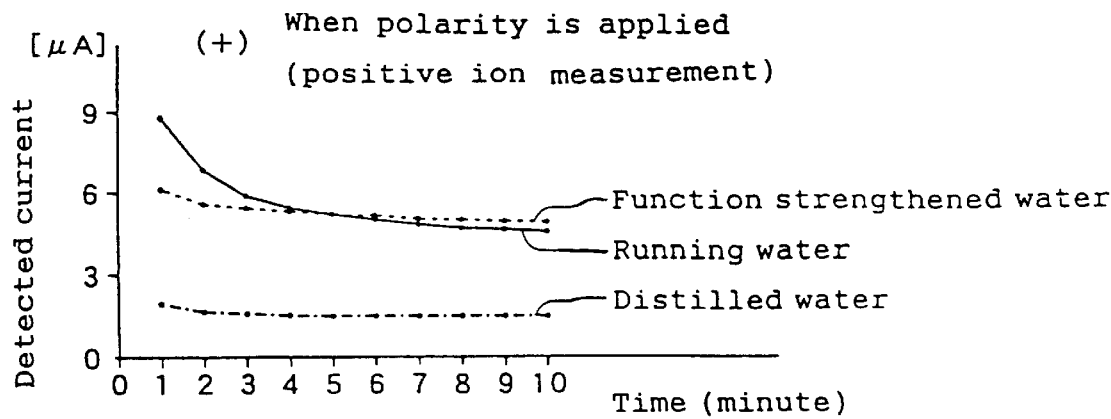
FIG. 5 is a graph of an experiment showing an experimental example of the invention.
Figure 5B:
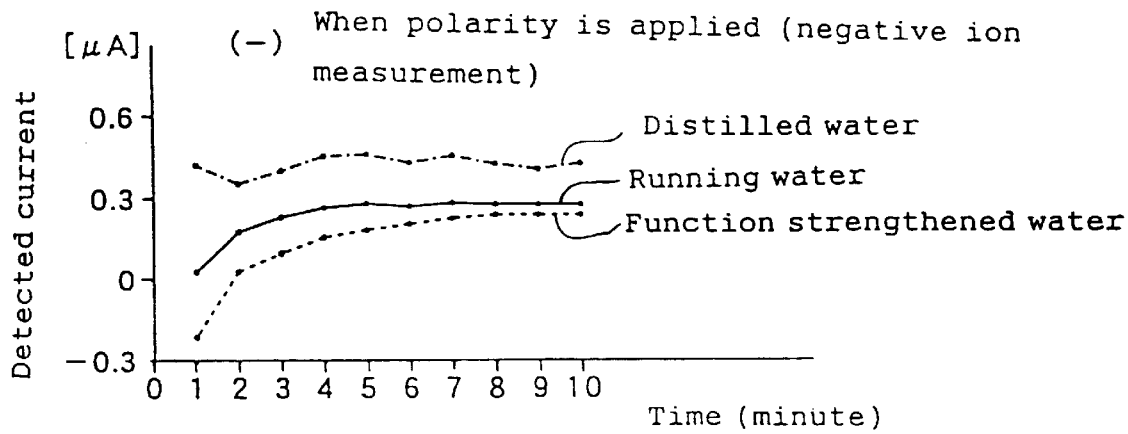
Figure 5C:
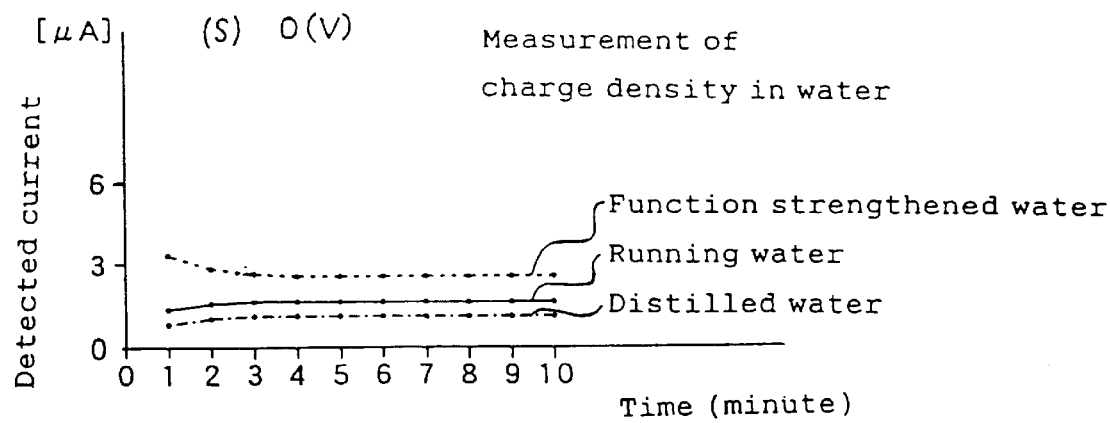

FIG. 5 shows results of measurements of distilled water as reference water, running water, water whose function is strengthened, and positive ions and negative ions in these water. As apparent from FIGS. 5A, 5B and 5C, a difference of amount of positive ions and negative ions in these water can be detected precisely.

Numerous modifications and alternative embodiments of the present invention will be apparent to those skilled in the art in view of the foregoing description. Accordingly, this description is to be construed as illustrative only, and is provided for the purpose of teaching those skilled in the art the best mode of carrying out the invention. The details of the structure and/or function can be varied substantially without departing from the spirit of the invention and all modifications which come within the scope of the appended claims are reserved.

What is claimed is:

1. A detecting and analyzing apparatus for positive ions and negative ions in a liquid, comprising:
    a sensor section of a coaxial cylindrical structure and, having a collector electrode,
    a signal detecting section for outputting a signal proportional to an amount of ions in the liquid that is in contact with said collector electrode,
    a container for accommodating the liquid to be analyzed,
    a measuring body, and
    an impressed voltage generating section provided in the measuring body for impressing positive voltage and negative voltage to said sensor section, wherein
    said measuring body processes the signal output from said signal detecting section, thereby displaying in accordance with an amount of detected ions and storing data of detected ion amount, and said impressed voltage generating section capable of changing a voltage value, a waveform, and frequency of the impressed voltage output to said sensor section.

2. A detecting and analyzing apparatus of claim 1 further comprising a temperature control means having a temperature sensor to detect a temperature of the liquid in the container and a heater to heat the liquid.

3. A detecting and analyzing apparatus for positive ions and negative ions in a liquid, comprising:
    a signal detecting box including therein a sensor section of a coaxial cylindrical structure disposed in an upper portion of a body and having a collector electrode, a signal detecting section for outputting a signal proportional to an amount of ions in the liquid that is in contact with said collector electrode, and a hoisting and lowering bench disposed in a lower portion of said body for hoisting and lowering a container placed on said hoisting and lowering bench and accommodating the liquids to be analyzed with respect to said sensor section, and
    a measuring body including an impressed voltage generating section for impressing positive voltage and negative voltage to said sensor section and a display section for processing the signal output from said signal detecting section and displaying in accordance with an amount of detected ions, and having a storing function of the data, wherein
    said impressed voltage generating section is capable of changing a voltage value, a waveform, and frequency of the impressed voltage output to said sensor section.

4. The detecting and analyzing apparatus of claim 3 further comprising a temperature control means mounted to the hoisting and lowering bench and having a temperature sensor to detect temperature of the liquid and a heater to heat the liquid.

* * * * *